United States Patent [19]
Baughn et al.

[11] 3,987,194
[45] Oct. 19, 1976

[54] USE OF PLEUROMUTILIN DERIVATIVES FOR THE TREATMENT OF SWINE DYSENTERY

[75] Inventors: Charles O. Baughn, Flemington, N.J.; Wayne H. Linkenheimer, Washington Crossing, Pa.; William E. Brown, Princeton, N.J.

[73] Assignee: E. R. Squibb & Sons, Inc., Princeton, N.J.

[22] Filed: May 12, 1975

[21] Appl. No.: 576,911

[52] U.S. Cl. ............................................. 424/311
[51] Int. Cl.² ....................................... A61K 31/22
[58] Field of Search ........................... 424/305, 311

[56] References Cited
OTHER PUBLICATIONS

Egger et al., — Chem. Abst. vol. 79 (1973) p. 65901V.

Primary Examiner—Sam Rosen
Attorney, Agent, or Firm—Lawrence S. Levinson; Merle J. Smith; Donald J. Barrack

[57] ABSTRACT

Swine dysentery can be treated by the administration to swine suffering from the disease of an effective amount of octahydro-5,8-dihydroxy-4,6,9,10-tetramethyl-6-vinyl-3a,9-propano-3aH-cyclopentacycloocten-1(4H)-one,8-[[2-(diethylamino)ethyl]thio]acetate or octahydro-5,8-dihydroxy-4,6,9,10-tetramethyl-6-vinyl-3a,9-propano-3aH-cyclopentacycloocten-1(4H)-one,8-[[2-[4-(2-hydroxyethyl)-1-piperazinyl]ethyl]thio]acetate.

9 Claims, No Drawings

USE OF PLEUROMUTILIN DERIVATIVES FOR THE TREATMENT OF SWINE DYSENTERY

BACKGROUND OF THE INVENTION

Swine dysentery is a mucohemorrhagic, diarrheal disease that affects primarily weanling pigs, but may affect larger pigs. The disease is often referred to as bloody scours, bloody dysentery, hemorrhagic dysentery, and mucohemorrhagic diarrhea. The disease occurs in many swine-raising areas of the world.

Morbidity is usually greater than 90 percent in weanling pigs and mortality may reach 75 percent. Experimentally, swine dysentery may decrease the rate of weight gain twofold and decrease efficiency of feed conversion threefold, as compared with uninfected control pigs. The disease causes tremendous financial losses because of death and decreased rate of growth of infected swine.

The cause of swine dysentery is, as yet, ill defined. In the past, *Vibrio coli* was believed to be associated with the disease. More recently, a large spirochete *Treponema hyodysenteriae*, acting in association with other intestinal microorganisms, is thought to be the cause of the disease. At present, the only reliable method of experimental reproduction of the disease is to inoculate susceptible pigs with colonic mucosa and colonic contents of pigs acutely affected with the disease.

The outlook for successful prevention and control of swine dysentery has not been promising because no product previously approved for use in the United States has satisfactorily treated the disease. Many swine owners have ultimately had to depopulate, clean, disinfect, and restock when the disease became enzootic. It appears that any immunity that develops from natural infection is short lived, and little optimism is expressed concerning the early development of a useful immunologic agent or vaccine.

SUMMARY OF THE INVENTION

It is an object of this invention to provide an effective method of treating swine dysentery.

It is a further object of this invention to treat swine dysentery by the administration of an agent that can be added to the feed or drinking water of the swine or can be administered to the swine by injection.

These and other objects, that will be readily apparent to a person of ordinary skill in the art, are realized by the method of this invention. The method of this invention comprises administering to a swine infected with swine dysentery an effective amount of octahydro-5,8-dihydroxy-4,6,9,10-tetramethyl-6-vinyl-3a,9-propano-3aH-cyclopentacycloocten-1(4H)-one,8-[[2-diethylamino)ethyl]-thio]acetate or octahydro-5,8-dihydroxy-4,6,9,10-tetramethyl-6-vinyl-3a,9-propano-3aH-cyclopentacycloocten-1 (4H)-one,8-[[2-[4-(2-hydroxyethyl)-1-piperazinyl]ethyl]thio]-acetate. The compounds will hereinafter be referred to as 14-deoxy-14-[[2-diethylaminoethyl]mercaptoacetoxy]mutilin and 14-deoxy-14-[[2-[4-(2-hydroxyethyl)-1-piperazinyl]ethyl]mercaptoacetoxy]mutilin respectively.

DETAILED DESCRIPTION OF THE INVENTION

Swine can be effectively treated for swine dysentery by the administration of 14-deoxy-14-[[2-diethylaminoethyl]mercaptoacetoxy]mutilin or 14-deoxy-14-[[2-[4-(2-hydroxyethyl)-1-piperazinyl]ethyl]mercaptoacetoxy]-mutilin. The compounds can be used in the form of physiologically acceptable acid-addition salts. For the treatment of swine dysentery the compounds can be administered to a swine in an amount of from about 0.5 milligrams/kilogram of animal body weight/day to about 100 milligrams/kilogram of animal body weight/day, preferably from about 3 milligrams/kilogram of animal body weight/day to about 20 milligrams/kilogram of animal body weight.

The route of administration of the compounds is not critical. The compounds can be administered as part of the affected swine's feed ration or in its drinking water. Alternatively, the compounds can be administered by intramuscular injection. Conventional techniques can be employed for formulation of the compounds.

14-Deoxy-14-[[2-diethylaminoethyl]mercaptoacetoxy]mutilin, 14-deoxy-14-[[2-[4-(2-hydroxyethyl)-1-piperazinyl]ethyl]mercaptoacetoxy]mutilin, and their pharmaceutically acceptable acid-addition salts are known; see, for example, French Pat. No. 2,157,828, published on June 8, 1973. The French patent discloses that the pleuromutilin derivatives disclosed have anti-bacterial activity.

The following examples are specific embodiments of this invention.

EXAMPLE 1

Eighteen male and female pigs, 5 to 8 weeks of age, are weighed and 12 of the pigs infected orally with the colonic scrapings from a pig which has been acutely infected with swine dysentery. Darkfield microscopic examination of the infecting material shows numerous spirochetes (*T. hyodysenteriae*).

Immediately following infection, 6 of the infected pigs are randomly assigned to a pen and receive swine starter ration with 14-deoxy-14-[[2-[-(4-(2-hydroxyethyl)-1-piperazinyl]ethyl]mercaptoacetoxy]mutilin, maleate (1:1) added at the rate of 100 gram/ton of ration (0.011%). Treatment begins immediately following infection. The remaining 6 infected pigs received swine ration which is non-medicated. The 6 noninfected pigs serve as age and condition controls and also receive non-medicated swine starter ration.

The swine ration used in this experiment consists of the following:

| Ingredients | Pounds |
| --- | --- |
| Corn meal | 1311 |
| Wheat midds | 100 |
| Soybean | 405 |
| Menhaden meal | 40 |
| Dried whey | 50 |
| Calcium phosphate | 30 |
| Salt | 10 |
| Mineral mix[1] | 2 |
| Molasses | 50 |
| Vitamin mix[2] | 2 |
| | 2000 |

1. The swine mineral mix at 2 pounds per ton of starter ration adds the following trace minerals:

| | |
| --- | --- |
| Copper | 5.4 grams |
| Iron | 68.0 grams |
| Manganese | 18.2 grams |
| Zinc | 45.4 grams |
| Iodine | .2 grams |

2. The swine vitamin mix at 2 pounds per ton of starter ration adds the following vitamins:

| Vitamin A | 3000 IU |
|---|---|
| Vitamin D | 1000 IU |
| Vitamin E | 20 IU |
| Vitamin $B_{12}$ | 30 μg |
| Riboflavin | 3 mg |
| Pantothenic acid | 10 mg |
| Niacin | 20 mg |
| Choline | 200 mg |

Treatment continues for 13 days at which time all pigs are again weighed and rectal swabs obtained from all pigs to determine the presence of *T. hyodysenteriae*.

The results are summarized in Table 1 below. The data show that the infected non-treated controls lost a mean of 0.24 kilograms during the treatment period while the non-infected controls gained a mean of 3.99 kilograms. The pigs treated with 14-deoxy-14-[[2-[4-(2-hydroxyethyl)-1-piperazinyl]ethyl]mercaptoacetoxy]mutilin, maleate (1:1) had a mean gain of 3.60 kilograms which did not differ significantly from the mean gain of the noninfected pigs.

At the end of the test 4 out of 6 of the infected, non-treated pigs still harbored *T. hyodysenteriae* while the organism had been eliminated from all of the treated pigs.

| Ingredients | Pounds |
|---|---|
| Corn meal | 1311 |
| Wheat midds | 100 |
| Soybean | 405 |
| Menhaden meal | 40 |
| Dried whey | 50 |
| Calcium phosphate | 30 |
| Salt | 10 |
| Mineral mix[1] | 2 |
| Molasses | 50 |
| Vitamin mix[2] | 2 |
| | 2000 |

1. The swine mineral mix at 2 pounds per ton of starter ration adds the following trace minerals:

| Copper | 5.4 grams |
|---|---|
| Iron | 68.0 grams |
| Manganese | 18.2 grams |
| Zinc | 45.4 grams |
| Iodine | .2 grams |

2. The swine vitamin mix at 2 pounds per ton of starter ration adds the following vitamins:

| Vitamin A | 3000 IU |
|---|---|
| Vitamin D | 1000 IU |

Table I

| Treatment | % drug in diet | Mean body weight gain | Presence of treponema/total tested* |
|---|---|---|---|
| | | kg | |
| No infection, no treatment | none | 3.99 | 3/6 |
| Infected, 14-deoxy-14-[[2-[4-(2-hydroxyethyl)-1-piperazinyl]ethyl]mercaptoacetoxy]mutilin, maleate (1:1) treatment | 0.011 | 3.60 | 0/6 |
| Infected, no treatment | none | −0.24 | 4/6 |

*Presence of treponema determined by microscopic examination of simple smears prepared from rectal swabs taken at the termination of the test.

EXAMPLE 2

In a series of 7 tests 131 male and female pigs, 5 to 8 weeks of age, are weighed and 93 of the pigs infected orally with the colonic scrapings from a pig which has been acutely infected with swine dysentery. Darkfield microscopic examination of the infecting material shows numerous spirochetes (*T. hyodysenteriae*).

Immediately following infection, 49 of the infected pigs are randomly assigned to a pen and receive swine starter ration with 14-deoxy-14-[[2-diethylaminoethyl]mercaptoacetoxy]multilin, hydrogen fumarate added at the rate of 50, 100 and 200 grams/ton of ration (0.0055, 0.011 and 0.022 percent). Treatment begins immediately following infection. The remaining 44 infected pigs received swine starter ration which is non-medicated. The 38 noninfected pigs serve as age and condition controls and also receive non-medicated swine starter ration.

The swine starter ration used in this experiment consists of the following:

| Vitamin E | 20 IU |
|---|---|
| Vitamin $B_{12}$ | 20 μg |
| Riboflavin | 3 mg |
| Pantothenic acid | 10 mg |
| Niacin | 20 mg |
| Choline | 200 mg |

Treatment continues for 10 to 14 days at which time all pigs are again weighed and rectal swabs obtained from all pigs to determine the presence of *T. hyodysenteriae*.

The results are summarized in Table II below. The data show that the infected non-treated controls had an average daily weight gain of only 0.6% while the non-infected controls had an average daily weight gain of 3%. The pigs treated with 14-deoxy-14-[[2-diethylaminoethyl]-mercaptoacetoxy]multilin, hydrogen fumarate of a feed concentration of 50, 100 and 200 g/ton had a weight gain comparable to the noninfected untreated control group.

At the end of the test most of the infected nontreated pigs still harbored *T. hyodysenteriae* while the organism had been eliminated from most of the treated pigs.

Table II

| Treatment | drug concentration in diet | Adjusted mean daily weight gains | Presence of treponema/total tested |
|---|---|---|---|
| | gram/ton | | |
| No infection, no treatment | none | 3.0 | 5/38 |
| Infected, 14-deoxy-14-[[2-diethylaminoethyl]-mercaptoacetoxy]mutilin, hydrogen fumarate treatment | 50 | 2.9 | 3/32 |
| Infected, 14-deoxy-14-[[2-diethylaminoethyl]-mercaptoacetoxy]mutilin, hydrogen fumarate treatment | 100 | 2.4 | 0/11 |
| Infected, 14-deoxy-14-[[2-diethylaminoethyl]-mercaptoacetoxy]mutilin, hydrogen fumarate treatment | 200 | 2.7 | 0/6 |
| Infected, no treatment | none | 0.6 | 24/44 |

EXAMPLE 3

In a series of 7 tests 106 male and female pigs, 5 to 8 weeks of age, are weighed and 77 of the pigs infected orally with the colonic scrapings from a pig which has been acutely infected with swine dysentery. Darkfield microscopic examination of the infecting material shows numerous spirochetes (*T. hyodysenteriae*).

Immediately following infection, the pigs are assigned to a pen and receive swine starter ration.

The swine starter ration used in this experiment consists of the following:

| Ingredients | Pounds |
|---|---|
| Corn meal | 1311 |
| Wheat midds | 100 |
| Soybean | 405 |
| Menhaden meal | 40 |
| Dried whey | 50 |
| Calcium phosphate | 30 |
| Salt | 10 |
| Mineral mix[1] | 2 |
| Molasses | 50 |
| Vitamin mix[2] | 2 |
| | 2000 |

1. The swine mineral mix at 2 pounds per ton of starter ration adds the following trace minerals:

| | |
|---|---|
| Copper | 5.4 grams |
| Iron | 68.0 grams |
| Manganese | 18.2 grams |
| Zinc | 45.4 grams |
| Iodine | .2 grams |

2. The swine mineral mix at 2 pounds per ton of starter ration adds the following vitamins:

| | |
|---|---|
| Vitamin A | 3000 IU |
| Vitamin D | 1000 IU |
| Vitamin E | 20 IU |
| Vitamin $B_{12}$ | 20 µg |
| Riboflavin | 3 mg |
| Pantothenic acid | 10 mg |
| Niacin | 20 mg |
| Choline | 200 mg |

Signs of swine dysentery and the presence of Treponema organisms in rectal swabs appear 4 to 8 days after the infection is given. When the infection is established, water medicated with 14-deoxy-14-[[2-diethylaminoethyl]mercaptoxy]mutilin, hydrogen fumarate is given to 51 of the pigs for 5 days. Five pigs are given the drug in the drinking water at 0.036 percent, 10 pigs are given the drug in the drinking water at 0.0125 percent and 36 pigs are given the drug in the drinking water at 0.0045 percent. After the 5-day period of medication the test is terminated. The weight gains of all treatment groups were significantly greater than the infected untreated controls and the shedding of Treponema markedly reduced.

The results are summarized in Table III below.

Table III

| Treatment | drug concentration in drinking water | Adjusted mean daily weight gains | Presence of treponema/total tested |
|---|---|---|---|
| | weight % | % | |
| No infection, no treatment | none | 4.6 | 5/29 |
| Infected, 14-deoxy-14-[[2-diethylaminoethyl]mercaptoacetoxy]-mutilin, hydrogen fumarate treatment | 0.0045 | 3.6 | 1/36 |
| Infected, 14-deoxy-14-[[2-diethylaminoethyl]mercaptoacetoxy]-mutilin, hydrogen fumarate treatment | 0.0125 | 3.4 | 0/10 |
| Infected, 14-deoxy-14-[[2-diethylaminoethyl]mercaptoacetoxy-mutilin, hydrogen fuma- | | | |

Table III-continued

| Treatment | drug concentration in drinking water | Adjusted mean daily weight gains | Presence of treponema/total tested |
|---|---|---|---|
| rate treatment | 0.036 | 4.9 | 0/5 |
| Infected, no treatment | none | −2.6 | 24/26 |

EXAMPLE 4

Twenty five male and female pigs, 5 to 8 weeks of age, are weighed and 20 of the pigs infected orally with the colonic scrapings from a pig which has been acutely infected with swine dysentery. Darkfield microscopic examination of the infecting material shows numerous spirochetes (*T. hyodysenteriae*).

Immediately following infection, 15 of the infected pigs are randomly assigned to pens and receive swine starter ration.

The swine starter ration used in this experiment consists of the following:

| Ingredients | Pounds |
|---|---|
| Corn meal | 1311 |
| Wheat midds | 100 |
| Soybean | 405 |
| Menhaden meal | 40 |
| Dried whey | 50 |
| Calcium phosphate | 30 |
| Salt | 10 |
| Mineral mix[1] | 2 |
| Molasses | 50 |
| Vitamin mix[2] | 2 |
| | 2000 |

1. The swine mineral mix at 2 pounds per ton of starter ration adds the following trace minerals:

| Copper | 5.4 grams |
|---|---|
| Iron | 68.0 grams |
| Manganese | 18.2 grams |
| Zinc | 45.4 grams |
| Iodine | .2 grams |

2. The swine vitamin mix at 2 pounds per ton of starter ration adds the following vitamins:

| Vitamin A | 3000 IU |
|---|---|
| Vitamin D | 1000 IU |
| Vitamin E | 20 IU |
| Vitamin $B_{12}$ | 20 μg |
| Riboflavin | 3 mg |
| Pantothenic acid | 10 mg |
| Niacin | 20 mg |
| Choline | 200 mg |

Signs of swine dysentery and the presence of Treponema organisms in rectal swabs appear 4 to 8 days after the infection is given. When the infection is established, 5 pigs each receive a single intramuscular injection of 14-deoxy-14-[[2-diethylaminoethyl]mercaptoacetoxy]mutilin, hydrogen fumarate at dosage levels of 10, 25 and 50 milligrams per kilogram of body weight.

The results are summarized in Table IV. The treatment prevented weight loss when compared with the infected untreated controls and markedly reduced the shedding of Treponema. None of the infected untreated pigs survived the 23-day test period.

Table IV

| Treatment | drug dosage mg/kg of body weight | Adjusted mean daily weight gains % | | Presence of treponema/ total tested | |
|---|---|---|---|---|---|
| | | 6 days after treatment | 23 days after treatment | 6 days after treatment | 23 days after treatment |
| No infection, no treatment | 0 | 1.6 | 9.23 | 0/5 | 0/5 |
| Infected, 14-deoxy-14-[[2-diethylamino-ethyl]mercaptoacetoxy]-mutilin, hydrogen fumarate treatment | 10 | 1.08 | 5.22 | 0/5 | 1/5 |
| Infected, 14-deoxy-14-[[2-diethylamino-ethyl]mercaptoacetoxy]-mutilin, hydrogen fumarate treatment | 25 | 2.15 | 8.36 | 0/5 | 0/5 |
| Infected, 14-deoxy-14-[[2-diethylamino-ethyl]mercaptoacetoxy-mutilin, hydrogen fumarate treatment | 50 | 1.16 | 6.48 | 0/5 | 0/5 |
| Infection, no treatment | 0 | −1.09* | ** | 4/4* | ** |

*One pig died due to swine dysentery.
**All 5 pigs died due to swine dysentery.

What is claimed is:

1. A method for treating swine dysentery which comprises administering to an infected swine an effective amount of octahydro-5,8-dihydroxy-4,6,9,10-tetramethyl-6-vinyl-3a,9-propano-3aH-cyclopentacycloocten-1(4H)-one, 8-[[2-(diethylamino)ethyl]thio]acetate, or octahydro-5,8-dihydroxy-4,6,9,10-tetramethyl-6-vinyl-3a,9-propano-3aH-cyclopentacycloocten-1(4H)-one,8-[[2-[4-(2-hydroxyethyl)-1-piperazinyl]ethyl]thio]acetate or a pharmaceutically acceptable salt thereof.

2. A method in accordance with claim 1 wherein the compound administered is octahydro-5,8-dihydroxy-4,6,-9,10-tetramethyl-6-vinyl-3a,9-propano-3aH-cyclopentacycloocten-1 (4H)-one,8-[[2-(diethylamino)ethyl]thio]acetate, or a pharmaceutically acceptable salt thereof.

3. A method in accordance with claim 1 wherein the compound administered is octahydro-5,8-dihydroxy-4,6,-9,10-tetramethyl-6-vinyl-3a,9-propano-3aH-cyclopentacycloocten-1(4H)-one,8-[[2-[4-(2-hydroxyethyl)-1-piperazinyl]ethyl]-thio]acetate or a pharmaceutically acceptable salt thereof.

4. A method in accordance with claim 1 wherein the compound is administered in an amount of from 0.5 milligrams per kilogram of animal body weight per day to 100 milligrams per kilogram of animal body weight per day.

5. A method in accordance with claim 1 wherein the compound is administered in an amount of from 3 milligrams per kilogram of animal body weight per day to 20 milligrams per kilogram of animal body weight per day.

6. A method in accordance with claim 1 wherein the compound is administered orally.

7. A method in accordance with claim 1 wherein the compound is administered by injection.

8. A method in accordance with claim 6 which comprises first combining the compound with the swine's feed.

9. A method in accordance with claim 6 which comprises first combining the compound with the swine's drinking water.

* * * * *